US010118135B2

(12) United States Patent
Park et al.

(10) Patent No.: US 10,118,135 B2
(45) Date of Patent: Nov. 6, 2018

(54) VIRUS HYBRID SEPARATION FILM AND METHOD FOR MANUFACTURING SAME

(71) Applicant: KOREA INSTITUTE OF ENERGY RESEARCH, Daejeon (KR)

(72) Inventors: Chul-Ho Park, Gyeonggi-do (KR); Namjo Jeong, Daejeon (KR); Harim Bae, Incheon (KR); Jiyeon Choi, Jeju-do (KR); Seung Cheol Yang, Jeju-do (KR)

(73) Assignee: Korea Institute of Energy Research, Daejeon (KR)

( * ) Notice: Subject to any disclaimer, the term of this patent is extended or adjusted under 35 U.S.C. 154(b) by 135 days.

(21) Appl. No.: 14/896,495

(22) PCT Filed: Jun. 5, 2014

(86) PCT No.: PCT/KR2014/005005
§ 371 (c)(1),
(2) Date: Dec. 7, 2015

(87) PCT Pub. No.: WO2014/196826
PCT Pub. Date: Dec. 11, 2014

(65) Prior Publication Data
US 2016/0129402 A1      May 12, 2016

(30) Foreign Application Priority Data

Jun. 7, 2013    (KR) .................. 10-2013-0065349

(51) Int. Cl.
*B01D 69/02*      (2006.01)
*B01D 69/10*      (2006.01)
(Continued)

(52) U.S. Cl.
CPC .......... *B01D 69/144* (2013.01); *B01D 69/02* (2013.01); *B01D 69/10* (2013.01); *C08J 9/0004* (2013.01);
(Continued)

(58) Field of Classification Search
None
See application file for complete search history.

(56) References Cited

U.S. PATENT DOCUMENTS 7,820,426 B2    10/2010   Wang et al.
8,334,127 B2    12/2012   Wang et al.
(Continued)

FOREIGN PATENT DOCUMENTS

JP        11-90214 A      4/1999

OTHER PUBLICATIONS

Yong Man Lee et al., "Nanomesh-Structure Ultrathin Membranes Harnessing the Unidirectional Alignment of Viruses on a Graphene-Oxide Film", Advanced Materials, 2014, pp. 3899-3904, vol. 26.

*Primary Examiner* — Krishnan S Menon
(74) *Attorney, Agent, or Firm* — Rabin & Berdo, P.C.

(57) ABSTRACT

The present invention provides a virus hybrid separation film and a method for manufacturing the same, capable of improving selective permeability using nano-pores of a virus. The separation film according to the present invention comprises: a porous support layer; and an active layer, disposed on the porous support layer, for having a target material selectively permeate thereinto, wherein the active layer comprises: a plurality of virus assemblies having pores; and an impermeable supporter. The impermeable supporter is positioned between the plurality of virus assemblies and supports the virus assemblies.

3 Claims, 3 Drawing Sheets

(51) Int. Cl.
  *B01D 69/12* (2006.01)
  *C12N 7/00* (2006.01)
  *B82Y 5/00* (2011.01)
  *B01D 69/14* (2006.01)
  *C08J 9/00* (2006.01)

(52) U.S. Cl.
  CPC ............ *B01D 2325/02* (2013.01); *B82Y 5/00* (2013.01); *C12N 7/00* (2013.01); *C12N 2770/00031* (2013.01)

(56) References Cited

U.S. PATENT DOCUMENTS

| | | | |
|---|---|---|---|
| 2009/0029441 A1* | 1/2009 | Wang | B82Y 5/00 435/235.1 |
| 2011/0151542 A1 | 6/2011 | Wang et al. | |
| 2011/0240550 A1 | 10/2011 | Moore et al. | |
| 2011/0284456 A1* | 11/2011 | Brozell | B01D 69/122 210/500.21 |
| 2013/0143303 A1 | 6/2013 | Wang et al. | |

* cited by examiner

```
              Virus
                │
                ▼
   Self-assembly and stabilization (S10)
                │
                ▼
           Drying (S20)
                │
                ▼
   Mixing with non-permeable support (S30)
                │
                ▼
     Applying to porous support (S40)
                │
                ◄──── Aligning in perpendicular direction (S45)
                ▼
         Solidifying (S50)
                │
                ▼
  Treating with heat and organic solvent (S60)
```

FIG. 3

VIRUS HYBRID SEPARATION FILM AND METHOD FOR MANUFACTURING SAME

TECHNICAL FIELD

The present disclosure relates to a virus hybrid separation film, and to a method for manufacturing the same. More particularly, the present disclosure relates to a virus hybrid separation film that exhibits enhanced selective permeability based on viral nano-pores, and to a method for manufacturing the same.

BACKGROUND ART

With an annual market growth rate of 6.6% over decades, separation films are manufactured in various forms and find applications in a variety of fields including seawater desalination, power generation by salinity gradient, redox cells, fuel cells, etc. Now, separation films are divided into polymer, ceramic, and metal separation films according to the material type thereof, and two or more different types thereof may be used in combination according to purposes. The function of a separation film depends on the pore size thereof. That is, particles can permeate through a separation film if their size is smaller than a pore size of the separation film whereas particles larger than the pore size cannot permeate. In addition, since there is very close relationship between porosity and selective permeability, porosity is also regarded as a very important factor for selective separation.

According to pore size, separation films are classified into reverse osmosis, nanofiltration, microfiltration, and ultrafiltration films. Such separation films are manufactured into various forms according to material properties thereof.

At present, there are five known methods for manufacturing separation films. First, a sintering process is used in which material powder is placed in a module, heated to a temperature slightly lower than the melting point, and sintered under a pressure to give a microfiltration film with a thickness of 100~500 μm. However, the film manufactured in this process has a porosity of as low as 10~40%, and is heterogeneous in pore morphology with a broad pore size distribution.

Second, a drawing process is used for manufacturing separation films. In the drawing process, a flat-sheet membrane or a hollow fiber membrane made of a crystalline material (particular polymeric material) is drawn to provide porosity. According to this process, a non-crystalline portion is oriented in the drawing direction to form fine fibrils. In this process, the porosity of the separation film can be increased to up to 90% and the pore size can be controlled according to an extent of drawing. However, materials applicable to the drawing process are limited, and the separation film becomes non-uniform in pore size depending on the extent of drawing.

Third, a separation film can be manufactured using a track etching technique in which a high-energy beam is irradiated onto a polymer film. This technique can establish the most uniform pores, but is complex and limits a film thickness available for the radiation energy. In addition, the track etching technique cannot be applied to various separation films, as understood from the fact that thus far the technique has been applied only to polycarbonate and polyester films.

Fourth, a solvent exchange method is most frequently adopted for the preparation of hollow fibers. This method, which is a phase inversion membrane preparation method, takes advantage of the concept that polymers can precipitate by solvent/non-solvent exchange. This method enables porous hollow fiber membranes to be manufactured in a single process. In the solvent exchange method, phase separation and phase change can be uniformly controlled to some extent, but the membranes exhibit a relatively broad spectrum of pore size distributions. Although now popularly used for seawater desalination, hollow fiber membranes are found to have an ion permeability of 95% or less due to the broad pore size distribution. Further, the method, based on solvent phase separation, is limited for available solvents, which, in turn, makes it difficult to prepare separation films from various materials.

Finally, a thermally induced phase inversion process was developed to expand available materials. Because it utilizes heat rather than conventional phase inversion techniques in forming pores, the thermally induced inversion process can artificially control pore sizes. However, this process is also limited in forming uniform pore sizes.

The performance of a separation film entirely depends on its pore size, pore size distribution, and porosity. Capable as it is of achieving a narrow pore size distribution, a track etching technique is difficult to apply to mass production. The other techniques, although allegedly reported to allow for the formation of uniform pore sizes, are observed to form pores with a wide pore size distribution. Substantially, the films manufactured by the aforementioned techniques exhibit a selectivity of 95% or less. For use as drinking water, for example, the water must be perfectly free of harmful matter, but the term "a selectivity of 95%" means that the film cannot completely remove harmful matter. Thus, the formation of uniform pore sizes in separation films, although recognized by all manufacturers, is a great problem that has yet to be solved.

DISCLOSURE

Technical Problem

Accordingly, the present invention has been made keeping in mind the above problems occurring in the prior art, and an object of the present invention is to provide a novel separation film in which uniform viral structures act as pores, and a method for manufacturing the same.

It is another object of the present disclosure to provide a virus hybrid separation film, useful as an ion exchange membrane, in which electrical charges of viral channel are controlled by genetic manipulation or chemical treatment, thereby adjusting selective permeability for cations/anions The objects of the present invention are not limited to the foregoing, and other objects and advantages of the present invention will be more apparent in the following description. In addition, it is readily understood that the objects and advantages of the present invention can be achieved by the means described in the claims and a combination thereof.

Technical Solution

In accordance with an aspect thereof, the present disclosure provides a separation film, comprising: a porous support layer; and an active layer, disposed on the porous support layer and having selective permeability for a target material, wherein the active layer comprises a plurality of virus assemblies having pores, and the impermeable support is positioned between the plurality of virus assemblies and functions to support the virus assemblies In some particular embodiments, each of the virus assemblies may have a cylindrical structure extended in a one-dimensional pattern. Also, the virus assemblies may be aligned in a direction perpendicular to the porous support layer. Further, the virus assemblies may be electrically charged in a controllable manner for selective permeation for cations or anions. In addition, the virus assemblies may be individually replaced by at least one porous structure selected from among a protein structure, a carbohydrate structure, and a lipid structure.

In accordance with another aspect thereof, the present disclosure provides a method for manufacturing a separation film, comprising: forming a plurality of virus assemblies having pores; mixing the plurality of virus assemblies with an impermeable support to give an active layer mixture; and applying the active layer mixture onto a porous support layer.

In some particular embodiments, the method may further comprise aligning the virus assemblies of the active layer mixture in a direction perpendicular to the support layer. Also, the method may further comprise solidifying the active layer mixture. Moreover, the method may further comprise subjecting viruses to self-assembly. In this regard, the self-assembly may be carried out by immersing the viruses in a solution having a pH of less than 4.

Advantageous Effects

As described hitherto, the present disclosure provides a separation film having nano-/micro-channels permeable for target materials, the separation film being based on highly uniform pores of viruses. In addition, various separation films can be fabricated by controlling pore sizes and surface charges of viruses through genetic engineering or chemical treatment or by employing varying kinds of viruses. Based on mixing with viruses, moreover, the method of the present disclosure is very simple, which leads to a significant reduction in production cost.

DESCRIPTION OF DRAWINGS

FIG. 3 is a flow chart of the manufacturing method.

Figure 1:
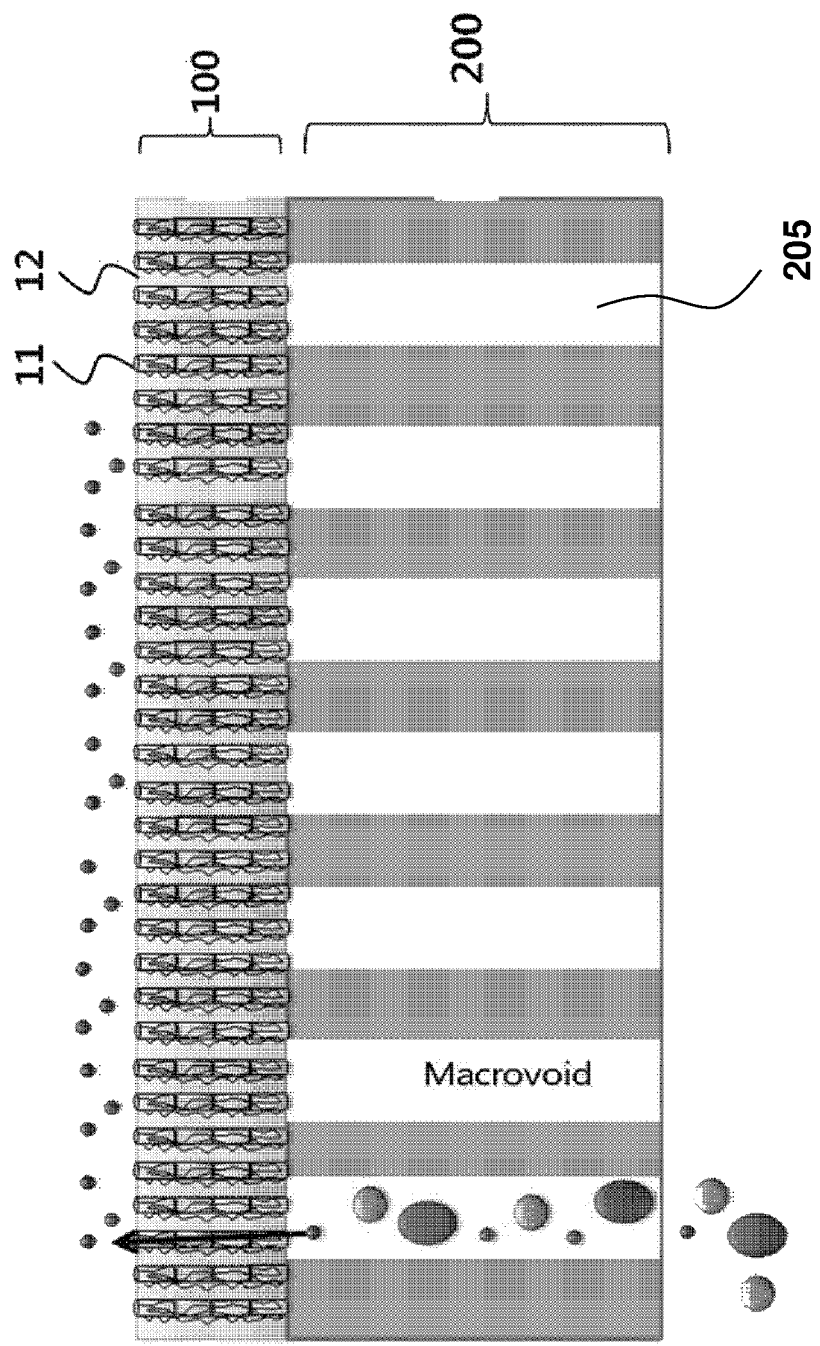
FIG. 1 is a schematic view illustrating a structure of a virus hybrid separation membrane according to an embodiment of the present disclosure.

<Description of the Reference Numerals in the Drawings>

| | |
|---|---|
| 10: tobacco mosaic virus | 11: virus assemblies |
| 12: impermeable support | 100: active layer |
| 200: porous support (layer) | |

BEST MODE

Reference now should be made to the drawings, throughout which the same reference numerals are used to designate the same or similar components. Below, a description will be given of preferred embodiments of the present invention in conjunction with the accompanying drawings. Throughout the accompanying drawings, the same reference numerals are used to designate the same or similar components. It should be apparent to those skilled in the art that although many specified elements such as concrete components are elucidated in the following description, they are intended to aid the general understanding of the invention and the present invention can be implemented without the specified elements. Further, in the description of the present invention, when it is determined that the detailed description of the related art would obscure the gist of the present invention, the description thereof will be omitted.

Figure 2:
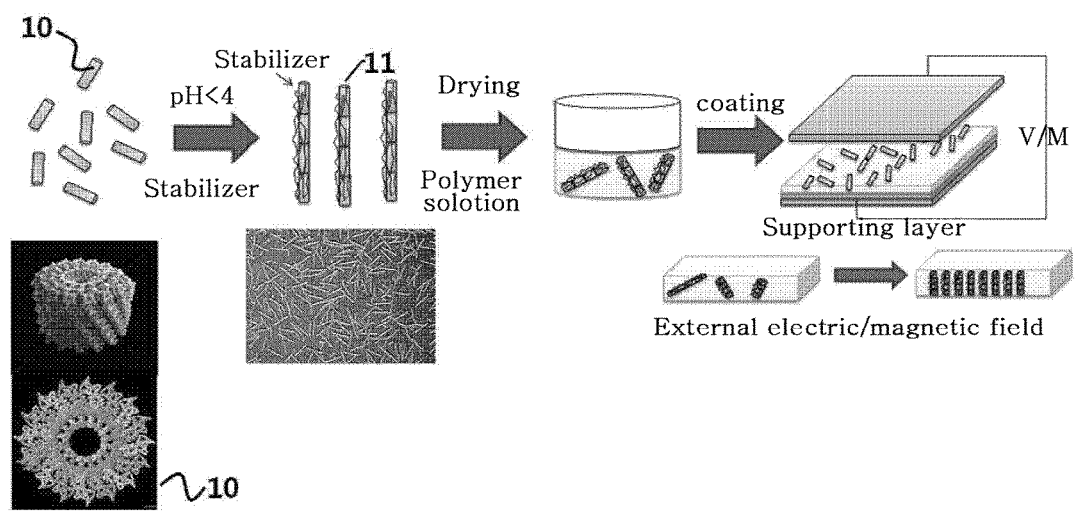
FIG. 2 is a view illustrating in a step-wise manner a manufacturing method of a virus hybrid separation film according to an embodiment of the present disclosure.

First, elucidation is made of a structure of a virus hybrid separation film in accordance with some embodiments of the present disclosure with reference to FIGS. 1 and 2. FIG. 1 is a schematic view illustrating a structure of a virus hybrid separation membrane according to an embodiment of the present disclosure. FIG. 2 is a view illustrating in a step-wise manner a manufacturing method of a virus hybrid separation film according to an embodiment of the present disclosure.

A virus consists essentially of proteins and a gene, such as RNA, etc., and there are various nano/micro structures according virus types. As can be seen in FIG. 2, when viruses with a cylindrical structure are simply mixed with a separation film support, internal pores of the cylindrical virus coat proteins and serve as pores of a separation film.

Thus, as shown in FIG. 1, the separation film according to some embodiments of the present disclosure comprises a porous support layer 200, and an active layer 100, disposed on the porous support layer and having selective permeability for a target material, wherein the active layer comprises a plurality of virus assemblies 1 having pores, and an impermeable support 12, and the impermeable support is positioned between the plurality of virus assemblies and supports the virus assemblies. Particularly, the active layer is about 200 nm thick, and may range in thickness from ones nm to ones μm in consideration of strength and resistance.

In some embodiments of the present disclosure, the virus hybrid separation film is a separation film based on a tobacco mosaic virus, which infects a wide range of plants. As can be seen in FIG. 2, a tobacco mosaic virus 10 has a cylindrical structure. Its capsid is made from 2130 molecules of a coat protein and one molecule of genomic RNA, 6390 bases long. The coat protein self-assembles into the rod-like helical structure around the RNA, which forms a hairpin loop structure. The protein monomer consists of 158 amino acids that are assembled into four main alpha-helices, which are joined by a prominent loop proximal to the axis of the virion. Virions are about 300 nm in length and about 18 nm in diameter.

The virus assemblies that serve as a channel in the separation film are made at a pH of 4 or less, and the pores of virus are connected in a one-dimensional pattern. In order to enhance self-assemblage, the virus assemblies may comprise a stabilizer and a crosslinking agent. In some embodiments of the present disclosure, the stabilizer may be PSS (polystyrene sulfonate) and the crosslinking agent may be glutaraldehyde. Further, the virus surface may be coated with polyaniline to reinforce the virus assemblies.

For use in the present disclosure, the virus may be wild type-tobacco mosaic virus (wt-TMV). Alternatively, the virus may be modified by chemical treatment or genetic manipulation. For wt-TMV, polymerization is conducted in the presence of aniline and ammonium persulfate in a solution to coat the virus surface with polyaniline, thereby enhancing the efficiency of self-assembly. PSS is further added to the viral solution to increase the stability of virus. By adjusting the reaction time, the length of virus assemblies can be controlled. Self-assembled viruses can be classified by length using electrophoresis, which makes it possible to control a concentration of virions in the solution.

For TMV-his that is prepared by attaching hexa-histidine to the surface of wt-TMV, pH or phosphate buffer concentrations are controlled to induce self-assembly into lamellas or multilayered lamellas as well as rods or fibers. In case of TMV-1cyc, a kind of TMV that has cysteine attached to the surface thereof, TMV rods can be aligned perpendicularly to an Au-coated substrate. This arrangement may be useful for establishing an active layer having nanopores in the thickness direction.

As shown in FIG. 1, gaps between virus assemblies 11 are filled with an impermeable support. The impermeable support 12 that accounts, together with the virus assemblies, for the active layer may be made of a polymer or a ceramic material. Materials pass across the separation film only via the pores of the virus assemblies 11 because the impermeable support blocks other routes. As long as it shows proper impermeability with mechanical strength according to use, any impermeable support may be employed in the present disclosure.

Here, the impermeable support may be made of an inorganic oxide, examples of which include titanium oxide, lead oxide, zirconium oxide, nickel oxide, copper oxide, yttrium (Y) oxide, magnesium oxide, calcium oxide, aluminum oxide, boron oxide, silicon oxide, and zeolite.

Alternatively, the impermeable support may be made of a thermoplastic resin, examples of which include polyamide, polyethylene, polyester, polyisobutylene, polytetrafluoroethylene, polypropylene, polyacrylonitrile, polysulfone, polyethersulfone, polycarbonate, polycarbonate, polyethylene terephthalate, polyimide, polyvinylene fluoride, polyvinyl chloride, cellulose acetate, cellulose diacetate, and cellulose triacetate.

Further, a curable resin may be used to form the impermeable support, and may be selected from a thermosetting resin, a photocurable resin, and a combination thereof. So long as it is well known in the art, any thermosetting or photocurable resin may be used in the present disclosure. For example, a thermosetting resin such as polydimethylsiloxane (PDMS), or a photocurable resin that can be cured by electromagnetic waves, such as a UV-curable resin, may be employed. Examples of the UV-curable resin include polyurethane-, polyacetylate-, polyepoxy-, polyurethaneacrylate-, polyesteracrylate-, polyepoxyacrylate-, and silicone-based UV curable resins.

An impermeable support made of polyamide may be fabricated by interfacial polymerization. For instance, ethylene diamine (ED) is dissolved in a virus solution on which a hexane layer containing trimesoyl chloride (TMC) is then placed to induce polymerization into a polyamide film at the interface between the aqueous layer and the hexane layer. A polyamide film may be obtained from various diamine materials as well as ED.

In the case where an electrospun fiber is used as a support, it is immersed in an ED solution containing viral self-assemblies. After removal of the surplus solution from the support with an air knife, a TMC solution in hexane is added to the ED on the support to induce an interfacial polymerization into a polyamide as an active layer. The thickness of the active layer can be controlled to range from hundreds of nanometers to ones of micrometers by adjusting the reaction time.

Plant viruses are stable even in organic solvents. Thus, when an organic solvent is slowly added to electrospun fibers that float on a dispersion of viruses, the polymer fibers are partially dissolved from the portions in contact with the solution, filling the gaps between the virus assemblies and thus serving as the active layer.

Meanwhile, when the direction of pores of the virus assemblies 11 coincides with that of pores 205 of the infra porous support, the virus hybrid separation film exhibits excellent performance. Hence, the virus assemblies should be aligned in a direction perpendicular to the infra porous support layer. To this end, the application of an electric field or a magnetic field during the manufacture of the separation film allows the virus assemblies 11 to be aligned in a direction perpendicular to the infra porous support layer.

When a concentration of nano-rods such as viral rod-like structures is controlled, the viruses can be aligned in the thickness direction at the interface between an aqueous dispersion of viruses and hexane. Under this condition, interfacial polymerization consolidates the virus assemblies in a direction perpendicular to the porous support. Also, application of an external electric field causes the virus assemblies to stand in a perpendicular direction within the active layer irrespective of the concentration of the virus assemblies. In this condition, interfacial polymerization on the surface of the support allows for the fabrication of high performance separation films having nanochannels in a direction perpendicular to the support layer.

The porous support 200 formed beneath the active layer 100 may be formed by casting a polymeric material on a non-woven fabric. Examples of materials for the non-woven fabric include, but are not limited to, polyester, polycarbonate, microporous polypropylene, polyphenylene ether, and polyvinylidene fluoride, with preference for polyester. The polymeric material may include polysulfone, polyethersulfone, polycarbonate, polyethylene oxide, polyimide, polyether imide, polyether ether ketone, polypropylene, polymethylpentene, polymethyl chloride, and polyvinylidene fluoride, but are not limited thereto, with preference for polysulfone.

The porous support layer may be fabricated by electrospinning. Electrospinning is a fiber production method that uses electric force to draw charged threads of polymer solutions or polymer melts up to fiber diameters in the order of some ten nanometers. For example, polyethersulfone (PED) nanofibers are produced by electrospinning a solution of PES/N,N-dimethylformamide at a temperature of 80° C. The non-woven fabric thus obtained is immersed in a solvent/non-solvent mixture to crosslink the fibers and thus to enhance the strength of the support. When using an electrospinning method, the porosity of the support layer can be controlled by adjusting a polymer concentration, a spinning rate, and a voltage. In order to enhance the strength of the fiber, the alignment of the electrosupn fiber is also controlled by adjusting the speed of the collector on which the electrospun fibers are collected.

Turning to FIGS. 2 and 3, an explanation is made of a method for manufacturing a virus hybrid separation film in accordance with some embodiments of the present invention. FIG. 2 is a schematic view of the manufacturing method of a virus hybrid separation film according to an embodiment of the present disclosure and FIG. 3 is a flow chart of the manufacturing method.

The method for manufacturing a virus hybrid separation film in accordance with some embodiments of the present disclosure comprises forming a plurality of virus assemblies having pores (S10); mixing the plurality of virus assemblies with an impermeable support to give an active layer mixture (S30); and applying the active layer mixture onto a porous support layer (S40). Given internal pores, any virus may be employed in the present disclosure. An example suitable for use in manufacturing a separation film in accordance with an embodiment of the present invention is tobacco mosaic virus.

Since viruses are negatively charged on their surfaces, electrical neutralization by decreasing pH triggers the self-assembly of the virus capsid (S10). Particularly, the pH of the virus solution is decreased to 4 or less. Also, a stabilizer may be added. A reversely charged polymer such as PSS (polystyrene sulfonate) may be employed. Through the self-assembly step (S10), virus assemblies 11 are fabricated in a 1D structural pattern. Herein, the term "1D structural pattern" means a cylindrical structure with pores connected linearly thereacross. The virus assemblies 11 may be fabricated into a linearly longer structure by controlling the reaction time.

After the self-assembly step (S10), the virus assemblies 11 are subjected to a drying step (S20). Optionally, the virus assemblies may be crosslinked with glutaraldehyde. The dried virus assemblies 11 are mixed with an impermeable support (S30). After the mixing step, the virus assemblies 11 are applied onto the porous support layer to a desired thickness using a coating method (S40). A virus hybrid separation film may be obtained by solidification (S50) just after the coating step (S40). However, alignment of the virus assemblies 11 perpendicular to the support layer 200 would endow the separation film with higher performance. To this end, an external electrical field or magnetic field is applied to the virus assemblies 11 so that they are oriented in a direction perpendicular to the infra porous support layer 200 (S45) before the solidification step (S50).

In addition, in order to remove pores that might be formed in the impermeable support 12 during the solidification (S50), a thermal treatment or a treatment with an organic solvent of gas phase (60) may be carried out.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A separation film, comprising:
   a porous support layer having a predetermined thickness and including a plurality of pores; and
   an active layer disposed on the porous support layer and having selective permeability for a target material, the active layer including
      a plurality of virus assemblies having pores, wherein each of the virus assemblies has a cylindrical structure with a predetermined length and has a pore formed along a central axis of the cylindrical structure, and
      an impermeable support,
   wherein the impermeable support is positioned between the plurality of virus assemblies and configured to support the virus assemblies such that the virus assemblies are retained by the impermeable support in a finished active layer, and
   the plurality of virus assemblies are arranged in the finished active layer such that the pores of the virus assemblies are aligned in a same direction with the direction of the pores of the porous support.

2. The separation film of claim 1, wherein the virus assemblies are aligned in a direction perpendicular to the porous support layer.

3. The separation film of claim 1, wherein the virus assemblies are charged in a controllable manner for selective permeation for cations or anions.

* * * * *